US012337150B2

(12) United States Patent
Belisle

(10) Patent No.: US 12,337,150 B2
(45) Date of Patent: Jun. 24, 2025

(54) AUTO INJECTOR WITH BI-STABLE CLUTCH PLATE

(71) Applicant: Phillips-Medisize A/S, Struer (DK)

(72) Inventor: Christopher Belisle, Somerset, WI (US)

(73) Assignee: Phillips-Medisize A/S, Struer (DK)

( * ) Notice: Subject to any disclaimer, the term of this patent is extended or adjusted under 35 U.S.C. 154(b) by 606 days.

(21) Appl. No.: 17/436,775

(22) PCT Filed: Mar. 23, 2020

(86) PCT No.: PCT/EP2020/057963
§ 371 (c)(1),
(2) Date: Sep. 7, 2021

(87) PCT Pub. No.: WO2020/193468
PCT Pub. Date: Oct. 1, 2020

(65) Prior Publication Data
US 2022/0176042 A1 Jun. 9, 2022

(30) Foreign Application Priority Data
Mar. 22, 2019 (EP) .................................... 19164529

(51) Int. Cl.
*A61M 5/315* (2006.01)
*A61M 5/20* (2006.01)
(Continued)

(52) U.S. Cl.
CPC ...... *A61M 5/31543* (2013.01); *A61M 5/2033* (2013.01); *A61M 5/3202* (2013.01);
(Continued)

(58) Field of Classification Search
CPC ............ A61M 5/2033; A61M 5/31543; A61M 5/3204; A61M 2005/14628; A61M 2005/2492; A61M 2005/3142
See application file for complete search history.

(56) References Cited

U.S. PATENT DOCUMENTS

2007/0173772 A1* 7/2007 Liversidge ............ A61M 5/326
604/192
2009/0247960 A1* 10/2009 Kohlbrenner .......... A61M 5/20
604/232
(Continued)

FOREIGN PATENT DOCUMENTS

CN 102770173 A 11/2012
CN 103492003 A 1/2014
(Continued)

OTHER PUBLICATIONS

International Preliminary Report on Patentability received for PCT Application No. PCT/EP2020/057963, mailed on Sep. 28, 2021, 7 pages.
(Continued)

*Primary Examiner* — Emily L Schmidt
*Assistant Examiner* — Samuel J Marrison

(57) ABSTRACT

An auto injector for delivery of a medicament to a patient is provided. The auto injector is adapted for receiving a cartridge assembly supporting a syringe. The auto injector includes a housing, a plunger, a plunger spring, and a clutch assembly. The plunger is movably positioned inside the housing. The plunger spring is adapted to move the plunger for delivery of the medicament. The clutch assembly is positioned inside the housing and includes a bi-stable clutch plate.

25 Claims, 14 Drawing Sheets

(51) Int. Cl.
*A61M 5/32* (2006.01)
*A61M 5/24* (2006.01)
*A61M 5/31* (2006.01)

(52) U.S. Cl.
CPC .............. *A61M 2005/2013* (2013.01); *A61M 2005/2407* (2013.01); *A61M 2005/2492* (2013.01); *A61M 2005/3142* (2013.01)

(56) References Cited

U.S. PATENT DOCUMENTS

| | | | |
|---|---|---|---|
| 2010/0262083 A1* | 10/2010 | Grunhut | A61M 5/2033 604/198 |
| 2010/0268170 A1* | 10/2010 | Carrel | A61M 5/2033 604/198 |
| 2013/0150800 A1 | 6/2013 | Kemp et al. | |
| 2013/0184651 A1* | 7/2013 | Avery | A61M 5/3135 604/246 |
| 2013/0310759 A1 | 11/2013 | Hourmand et al. | |
| 2016/0354556 A1* | 12/2016 | Zucker | A61M 5/326 |
| 2018/0169338 A1* | 6/2018 | Kemp | A61M 5/2033 |
| 2019/0374717 A1* | 12/2019 | Swanson | A61M 5/3202 |
| 2020/0038598 A1* | 2/2020 | Chu | A61M 5/3204 |
| 2022/0016356 A1* | 1/2022 | Alexandersson | A61M 5/3204 |

FOREIGN PATENT DOCUMENTS

| | | |
|---|---|---|
| CN | 108136119 A | 6/2018 |
| GB | 2493432 A | 2/2013 |
| WO | 2009040602 A1 | 4/2009 |
| WO | 2010125400 A2 | 11/2010 |
| WO | 2012000873 A1 | 1/2012 |

OTHER PUBLICATIONS

International Search Report and Written Opinion received for PCT Application No. PCT/EP2020/057963, mailed on Apr. 20, 2020, 9 pages.

* cited by examiner

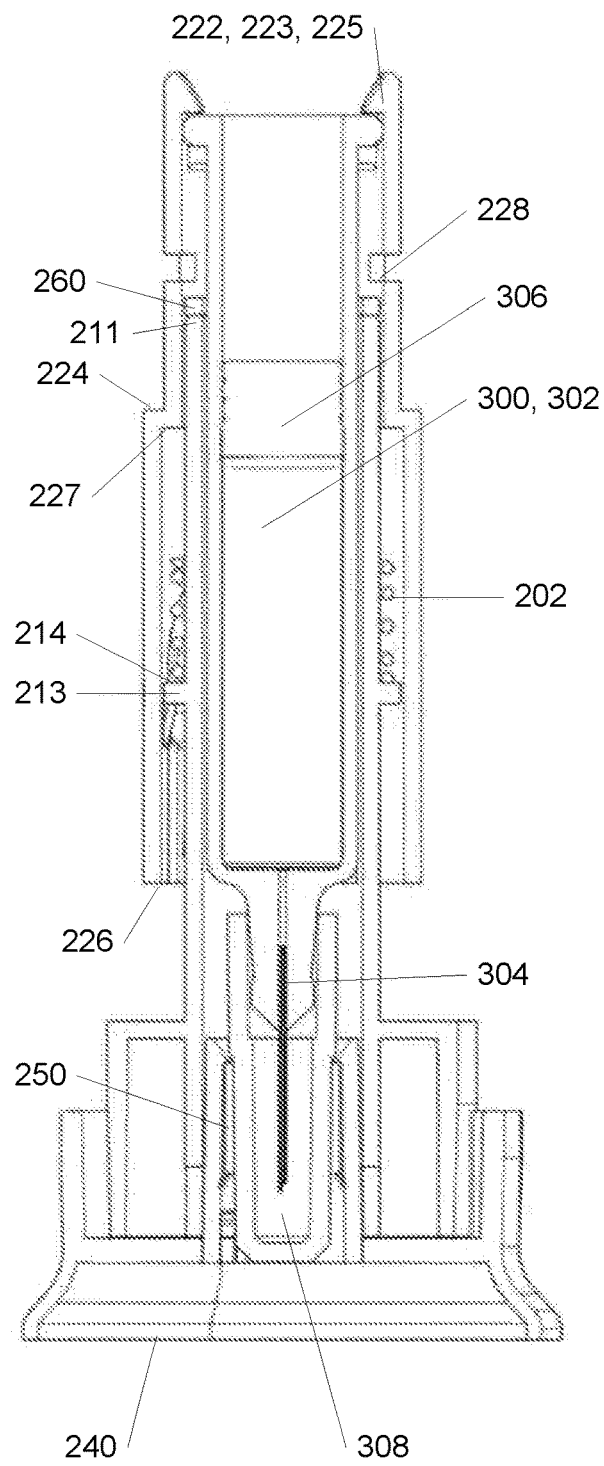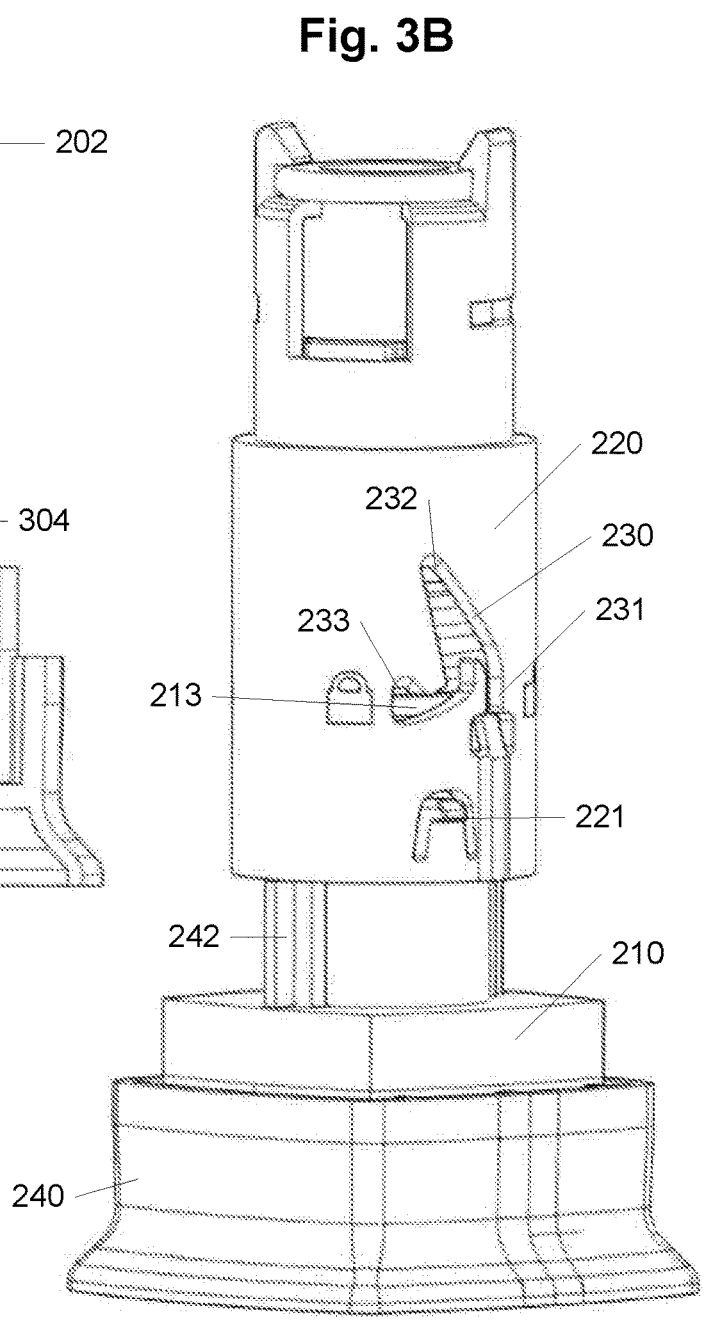
Fig. 3A
Fig. 3B

AUTO INJECTOR WITH BI-STABLE CLUTCH PLATE

The invention relates to an auto-injector with a bi-stable clutch plate.

RELATED APPLICATIONS

This application is a national phase of International Application No. PCT/EP2020/057963, filed Oct. 1, 2020, which claims priority to European Application No. 19164529.0, filed Mar. 22, 2019, which are incorporated herein by reference.

BACKGROUND

Auto injectors for the delivery of medicament to a patient comes in many varieties depending on the type of medicament, which is to be delivered to the patient.

SUMMARY

Disclosed herein is an auto injector for delivery of a medicament to a patient. The auto injector is extending from a proximal end to a distal end, wherein the auto injector is adapted for receiving a cartridge assembly supporting a syringe comprising:
  a syringe compartment containing the medicament;
  a hollow needle through which the medicament can be delivered to a patient;
  a stopper proximally movable inside the syringe compartment for evacuating the medicament in the syringe compartment;
  a syringe cap adapted for protecting the needle.

By proximal end is meant the end from where the needle protrudes during injection of medicament. By distal end is meant the end pointing in the opposite direction of the proximal end. The use of the naming proximal and distal is to be understood as not changing if a user flips the auto injector around as the naming refers to the directional orientation of the needle. A longitudinal direction in the auto injector and all its parts may be defined as extending between the proximal and distal end.

The auto injector may comprise:
  a housing;
  a plunger movably positioned inside the housing, the plunger being adapted for moving the stopper inside the syringe compartment proximally for delivery of the medicament;
  a plunger spring adapted for moving the plunger proximally for delivery of the medicament.

The auto injector may further comprise a clutch assembly position inside the housing. The clutch assembly may comprise a bi-stable clutch plate comprising a flexible ring part from where one or more retention arms extend, the flexible ring part being movable between:
  a first stable position where the one or more retention arms protrudes outwardly and engages with an inside surface of the housing, wherein the flexible ring part is in the first stable position during delivery of medicament, and
  a second stable position where the one or more retention arms protrudes inwardly and are disengaged from the inside surface of the housing
wherein upon translation of the cartridge assembly into the auto injector after delivery of the medicament, the clutch plate retention arms are brought into contact with release ribs inside the housing whereby the flexible ring part on the clutch plate is moved from the first stable position to the second stable position allowing the cartridge assembly to be removed and the auto injector to be reset.

By bi-stable clutch plate is meant a plate with two stable geometries, i.e. two stable positions, which maintains a stable geometry unless actively moved into the other stable geometry. Moving between the two stable geometries requires an active movement, e.g. contact between the clutch plate retention arms and release ribs inside the housing. Thus, the bi-stable clutch plate does not automatically switch from one stable position into the other stable position if no other parts are preventing it from doing so.

By the use of a bi-stable clutch plate, a compact and robust auto injector is obtained. The bi-stable clutch plate normally takes up very little space inside the auto injector proving the compactness. The above described auto injector is further very user friendly. As the bi-stable clutch plate does not switch from one stable position to the other stable position unless it comes into contact with parts actively moving between the two stable positions, the bi-stable clutch plate may grip the inside of the housing to hold the spring force of the compressed plunger spring during cartridge insertion and injection. This ensures that if the user stops compressing the housing onto the cartridge during use, a spring pressure is held by the clutch plate preventing release of spring pressure/part movement. Further, the bi-stable clutch plate facilitates an easy and safe cartridge installation, as the auto injector remains static if a user stops short of full insertion of the cartridge. This allows the auto injector to be stored both with the plunger spring extended and relaxed. It further allows for an easy reset of the auto injector.

The auto injector will normally be reusable. The cartridge assembly may be either a reusable item or a one-time use item, whereas the syringe is a one-time use item. By having two stable positions, the bi-stable clutch plate enables the auto-injector to be reset and ready for use with a new cartridge assembly and syringe.

BRIEF DESCRIPTION OF THE DRAWINGS

Various examples are described hereinafter with reference to the figures. Like reference numerals refer to like elements throughout. Like elements will, thus, not be described in detail with respect to the description of each figure. It should also be noted that the figures are only intended to facilitate the description of the examples. They are not intended as an exhaustive description of the claimed invention or as a limitation on the scope of the claimed invention. In addition, an illustrated example needs not have all the aspects or advantages shown. An aspect or an advantage described in conjunction with a particular example is not necessarily limited to that example and can be practiced in any other examples even if not so illustrated, or if not so explicitly described.

FIGS. 3A-B show the cartridge assembly of FIG. 2 with a syringe in a cut-through view (FIG. 3A) and a side view (FIG. 3B).

DETAILED DESCRIPTION

Figure 1A:
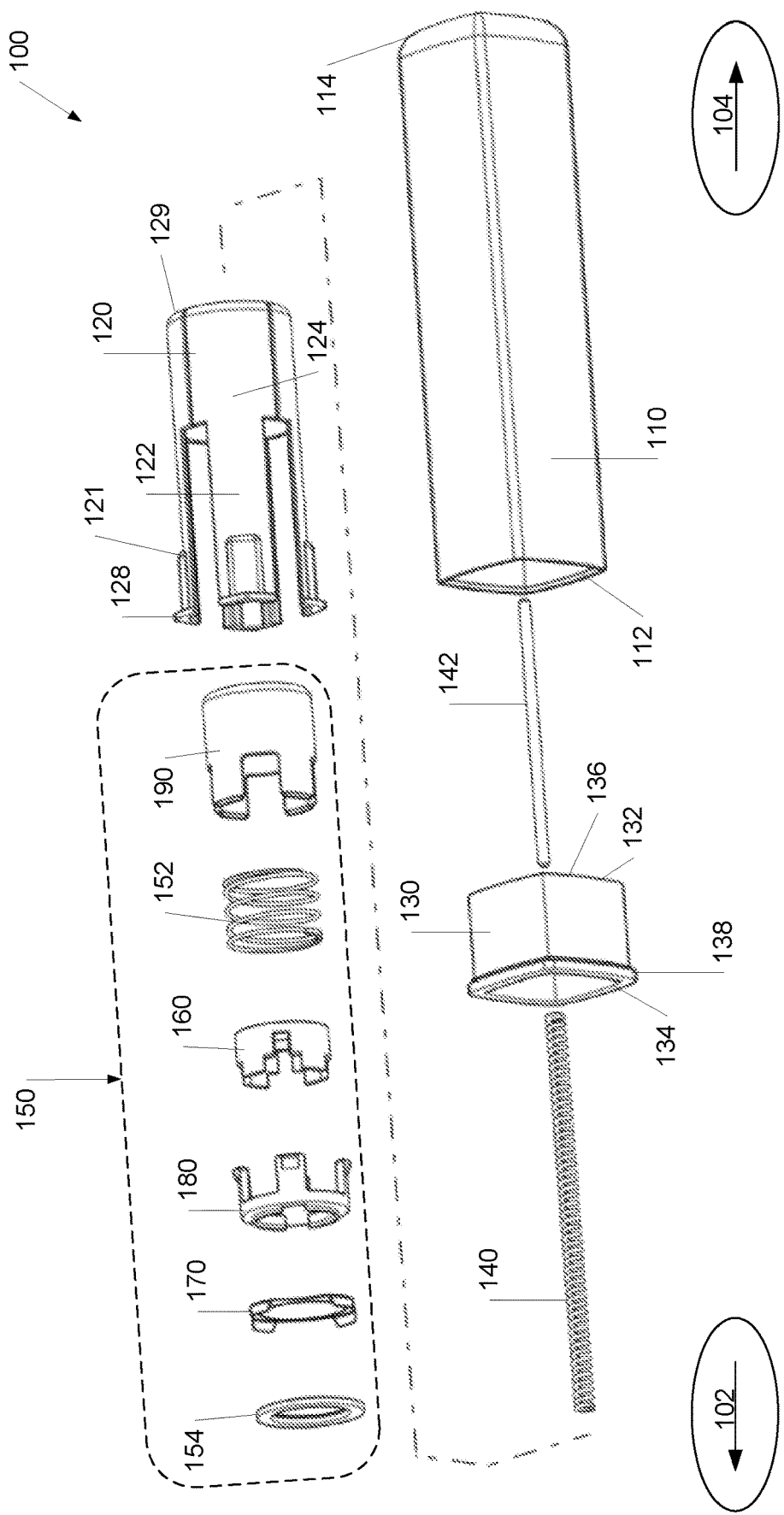
FIG. 1A shows an example of an auto injector in an exploded view.

Exemplary examples will now be described more fully hereinafter with reference to the accompanying drawings. In this regard, the present examples may have different forms and should not be construed as being limited to the descriptions set forth herein. Accordingly, the examples are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

In the drawings, thicknesses of a plurality of layers and areas are illustrated in an enlarged manner for clarity and ease of description thereof. When a layer, area, element, or plate is referred to as being "on" another layer, area, element, or plate, it may be directly on the other layer, area, element, or plate, or intervening layers, areas, elements, or plates may be present therebetween. Conversely, when a layer, area, element, or plate is referred to as being "directly on" another layer, area, element, or plate, there are no intervening layers, areas, elements, or plates therebetween. Further when a layer, area, element, or plate is referred to as being "below" another layer, area, element, or plate, it may be directly below the other layer, area, element, or plate, or intervening layers, areas, elements, or plates may be present therebetween. Conversely, when a layer, area, element, or plate is referred to as being "directly below" another layer, area, element, or plate, there are no intervening layers, areas, elements, or plates therebetween.

The spatially relative terms "lower" or "bottom" and "upper" or "top", "below", "beneath", "less", "above", and the like, may be used herein for ease of description to describe the relationship between one element or component and another element or component as illustrated in the drawings. It will be understood that the spatially relative terms are intended to encompass different orientations of the device in use or operation, in addition to the orientation depicted in the drawings. For example, in the case where a device illustrated in the drawings is turned over, elements described as being on the "lower" side of other elements, or "below" or "beneath" another element would then be oriented on "upper" sides of the other elements, or "above" another element. Accordingly, the illustrative term "below" or "beneath" may include both the "lower" and "upper" orientation positions, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below, and thus the spatially relative terms may be interpreted differently depending on the orientations described.

Throughout the specification, when an element is referred to as being "connected" to another element, the element is "directly connected" to the other element, or "electrically connected" to the other element with one or more intervening elements interposed therebetween.

The terminology used herein is for the purpose of describing particular examples only and is not intended to be limiting. As used herein, the singular forms "a," "an," and "the" are intended to include the plural forms, including "at least one," unless the content clearly indicates otherwise. "At least one" is not to be construed as limiting "a" or "an." It will be further understood that the terms "comprises," "comprising," "includes" and/or "including," when used in this specification, specify the presence of stated features, integers, steps, operations, elements, and/or components, but do not preclude the presence or addition of one or more other features, integers, steps, operations, elements, components, and/or groups thereof.

It will be understood that, although the terms "first," "second," "third," and the like may be used herein to describe various elements, these elements should not be limited by these terms. These terms are only used to distinguish one element from another element. Thus, "a first element" discussed below could be termed "a second element" or "a third element," and "a second element" and "a third element" may be termed likewise without departing from the teachings herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Unless otherwise defined, all terms used herein (including technical and scientific terms) have the same meaning as commonly understood by those skilled in the art to which this invention pertains. It will be further understood that terms, such as those defined in commonly used dictionaries, should be interpreted as having a meaning that is consistent with their meaning in the context of the relevant art and will not be interpreted in an idealized or overly formal sense unless expressly so defined in the present specification.

Exemplary examples are described herein with reference to cross section illustrations that are schematic illustrations of idealized examples, wherein like reference numerals refer to like elements throughout the specification. As such, variations from the shapes of the illustrations as a result, for example, of manufacturing techniques and/or tolerances, are to be expected. Thus, examples described herein should not be construed as limited to the particular shapes of regions as illustrated herein but are to include deviations in shapes that result, for example, from manufacturing. For example, a region illustrated or described as flat may have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims. Some of the parts which are not associated with the description may not be provided in order to specifically describe exemplary examples of the present disclosure.

Disclosed herein is an auto injector for delivery of a medicament to a patient. The auto injector is extending from a proximal end to a distal end, wherein the auto injector is adapted for receiving a cartridge assembly supporting a syringe comprising:

- a syringe compartment containing the medicament;
- a hollow needle through which the medicament can be delivered to a patient;
- a stopper proximally movable inside the syringe compartment for evacuating the medicament in the syringe compartment;
- a syringe cap adapted for protecting the needle.

The auto injector may comprise:
- a housing;
- a plunger movably positioned inside the housing, the plunger being adapted for moving the stopper inside the syringe compartment proximally for delivery of the medicament;
- a plunger spring adapted for moving the plunger proximally for delivery of the medicament.

The auto injector may further comprise a clutch assembly position inside the housing. The clutch assembly may comprise a bi-stable clutch plate comprising a flexible ring part from where one or more retention arms extend, the flexible ring part being movable between:
- a first stable position where the one or more retention arms protrudes outwardly and engages with an inside surface of the housing, wherein the flexible ring part is in the first stable position during delivery of medicament, and
- a second stable position where the one or more retention arms protrudes inwardly and are disengaged from the inside surface of the housing wherein upon translation of the cartridge assembly into the auto injector after delivery of the medicament, the clutch plate retention arms are brought into contact with release ribs inside the housing whereby the flexible ring part on the clutch plate is moved from the first stable position to the second stable position allowing the cartridge assembly to be removed and the auto injector to be reset.

In one or more examples, the clutch assembly comprises a clutch release sleeve comprising a ring shaped part with a distal surface from where release sleeve arms extends.

In one or more examples, the clutch assembly comprises a clutch lock ring comprising a first proximal clutch lock ring surface, and a second proximal clutch lock ring surface, wherein the distal surface of the clutch release sleeve are adapted for abutting the first proximal clutch lock ring surface in a first position and the second proximal clutch lock ring surface in a second position. The clutch lock ring may further comprise a third proximal clutch lock ring surface. The second proximal clutch lock ring surface is normally position between the first ad the third proximal clutch lock ring surface. The three proximal clutch lock ring surfaces may form a three stair case step geometry where the proximal clutch lock ring surfaces are positioned to point in the proximal direction perpendicular in relation to the longitudinal axis of the clutch lock ring.

In one or more examples, the clutch plate is in the first stable position when the cartridge assembly and the auto injector are moved towards each other. The one or more retention arms engaging the inside surface of the housing are in this one or more examples ensuring that a spring pressure is held by the clutch plate preventing movement of the clutch assembly within the housing, should the relative movement between the cartridge assembly and the auto injector towards each other stop. Unintentional reset of the auto injector is thereby avoided.

In one or more examples, the auto injector further comprises a housing collar positioned at the proximal end of the housing partly extending inside the housing.

In one or more examples, the housing collar comprises a housing collar retention shelf at its distal end, the housing collar retention shelf being adapted for locking the cartridge assembly to the auto injector when the cartridge assembly is fully inserted into the auto injector.

In one or more examples, the clutch assembly further comprises a clutch retainer positioned between the clutch plate and the cartridge assembly when the cartridge assembly is contained in the auto injector.

In one or more examples, the plunger spring is contained inside an inner plunger tube part.

In one or more examples, the auto injector further comprises a plunger spring pin connected to the housing and extending inside the inner plunger tube part, wherein the plunger spring is surrounding the plunger spring pin.

In one or more examples, the auto injector is adapted for receiving a cartridge assembly into the proximal end of the auto injector.

In one or more examples, when the cartridge assembly and the auto injector are moved towards each other, the clutch assembly and the plunger are moved in the distal direction relative to the housing whereby the plunger spring is compressed.

In one or more examples, the release sleeve arms on the release sleeve are further pressing against a proximal plunger surface of the plunger in a first position. The auto injector is normally in this first position during insertion of the cartridge into the auto injector and during insertion of the needle into the patient. The release sleeve arms on the release sleeve may disengage from the proximal plunger surface of the plunger in a second position in which the plunger moves proximally for delivery of medicament.

In one or more examples, the clutch lock ring comprises a first proximal clutch lock ring surface, a second proximal clutch lock ring surface, and a third proximal clutch lock ring surface. The distal surface of the clutch release sleeve are normally adapted for abutting the first proximal clutch lock ring surface in a first position and the second proximal clutch lock ring surface in a second position.

In one or more examples, the clutch lock ring is movable in the distal direction relatively to the release sleeve upon movement of the cartridge assembly distally within the auto injector.

In one or more examples, the release sleeve arms of the clutch release sleeve are adapted for flexing inward upon disengagement of the clutch lock ring from the release sleeve. This allows the plunger to move proximally for delivery of medicament.

In one or more examples, the release sleeve arms are adapted for being secured in a locking opening in the cartridge assembly when flexing inward thereby locking the cartridge assembly and the release sleeve together. This ensures that the plunger can move the stopper inside the syringe compartment proximally for delivery of the medicament while the syringe compartment is kept in the same position inside the injector.

Thus, in one or more examples, when the release sleeve arms of the clutch release sleeve flex inward, the plunger is released thereby enabling the plunger spring to move the plunger proximally for delivery of the medicament.

In one or more examples, the auto injector further comprises:
- a clutch cap comprising a first proximal clutch cap surface abutting the distal surface on the ring shaped part of the clutch release sleeve; and
- a clutch reset spring positioned inside the clutch cap exerting a pressure on the clutch cap and the clutch lock ring.

The first proximal clutch cap surface and the distal surface on the ring shaped part of the clutch release sleeve may also be locked together, e.g. by a welding of the two parts together.

In one or more examples, the clutch lock ring is adapted for compressing the clutch reset spring when the lock ring is moved in the distal direction upon movement of the cartridge assembly for delivery of the medicament.

In one or more examples, the clutch reset spring is adapted for pushing the clutch lock ring towards the release sleeve arms after removal of the used syringe. This resets the clutch assembly.

In one or more examples, the cartridge assembly is movable into the auto injector after delivery of medicament. Normally, upon removal of the auto injector from the patient's skin after end delivery of medicament, the cartridge assembly is locked in a position, where asses to the needle is prevented. The movement of the cartridge assembly into the auto injector may therefore be obtained by a user manually pressing the cartridge assembly into the auto injector as assess to the needle inside the cartridge has been prevented.

In one or more examples, during translation of the cartridge assembly into the auto injector, the clutch plate retention arms are brought into contact with release ribs inside the housing whereby the flexible ring part on the clutch plate is moved from the first stable position to the second stable position. In the second stable position, the cartridge assembly is not maintained fixed to the auto injector by the clutch plate. Thus, the cartridge assembly may is allowed to be removed from the injector after injection of medicament.

In one or more examples, the clutch assembly moves distally upon removal of the removal of the cartridge assembly. The clutch plate may be in the second stable position during this distal movement. The clutch assembly moves distally with the cartridge assembly as the release sleeve arms of the clutch release sleeve flex inward locking the release sleeve arms and thereby the clutch assembly in a locking opening in the cartridge assembly. As the release sleeve arms of the clutch release sleeve passes the proximal plunger surface inside the plunger, the release sleeve arms flexes outwards. This unlocks the cartridge assembly from the clutch assembly whereby the cartridge assembly can be fully removed from the auto injector. The clutch plate may further come in contact with features inside the housing when moving proximally upon removal the cartridge assembly. The features inside the housing may move the one or more retention arms from the second stable position to the first stable position.

In one or more examples, the cartridge assembly is adapted for supporting a syringe comprising:
- a syringe compartment containing the medicament;
- a hollow needle through which the medicament can be delivered to a patient;
- a stopper proximally movable inside the syringe compartment for evacuating the medicament in the syringe compartment;
- a syringe cap adapted for protecting the needle;

wherein the cartridge assembly comprises:
- a needle shroud comprising a hollow elongated tubular section adapted for receiving the syringe; and
- a lock tube extending around the tubular section of the needle shroud, the lock tube comprising a snap fit connection adapted for securing the syringe inside the lock tube and the needle shroud.

In one or more examples, the distal end of the lock tube comprises inwardly extending flanges, which locks the syringe inside the lock tube with the snap fit connection.

In one or more examples, the cartridge assembly further comprises a cartridge assembly cap and a grip tube, wherein the grip tube is positioned inside the cartridge assembly cap, and wherein the grip tube is adapted for capturing the syringe cap when the syringe is positioned inside the cartridge assembly.

In one or more examples, the cartridge assembly cap comprises distally protruding tabs abutting a proximal end of the lock tube thereby preventing proximal movement of the lock tube relative to the needle shroud when the cartridge assembly cap is connected with the needle shroud.

In one or more examples, the cartridge assembly cap and the grip tube are removable from the cartridge assembly after the cartridge assembly is fully inserted into the auto injector.

In one or more examples, the needle shroud is enabled for retracting into the housing when removing the cartridge assembly cap.

In one or more examples, depression of the housing proximally towards the needle shroud after removal of the cartridge assembly cap retracts the needle shroud into the housing.

In one or more examples, the lock tube comprises one or more retention snaps engaging on the housing collar retention shelf securing the lock tube inside the auto injector.

In one or more examples, upon depression of the housing, the lock tube comprising the syringe is adapted for moving proximally together with the housing enabling insertion of the needle. In one or more examples, upon depression of the housing the needle shroud is adapted for translating distally into the housing.

In one or more examples, the lock tube is adapted for at least partially rotating relatively to the housing as the needle shroud translates distally into the housing.

In one or more examples, upon depression of the housing, the needle shroud is adapted for rotating the lock tube relatively to the housing.

The plunger is normally released when the lock ring is moved distally within the clutch assembly. The lock ring is moved by the release collar, which in turn is normally moved by the needle shroud during needle insertion.

In one or more examples, after release of plunger, the lock tube is adapted for completing/continuing the rotation relatively to the housing whereby the one or more lock tube retention snaps are moved to a position allowing removal of the cartridge assembly from the auto injector.

In one or more examples, the lock tube comprises a lock tube channel and the needle shroud comprises a needle shroud protrusion movable inside the lock tube channel between:
- a first lock tube channel position,
- a second lock tube channel position, and
- a third lock tube channel position.

In one or more examples, the needle shroud protrusion is in the first lock tube channel position before removal of the cartridge assembly cap.

In one or more examples, the needle shroud protrusion is moved from the first lock tube channel position to the second lock tube channel position upon depression of the housing after removal of the cartridge assembly cap.

In one or more examples, the cartridge assembly further comprises a lock tube spring positioned between a peripheral distal needle shroud support surface and a proximal lock tube support surface.

In one or more examples, the lock tube spring is adapted for being compressed during delivery of the medicament, and for moving the needle shroud protrusion from the second lock tube channel position to the third lock tube channel position after delivery of the medicament decompresses.

In one or more examples, when the needle shroud protrusion is in the third lock tube channel position compression of the needle shroud relative to the lock tube is limited or even prevented.

In one or more examples, the needle shroud comprises a ring protrusion whereon the distal needle shroud support surface is, and whereon the needle shroud protrusion is positioned.

Referring now to FIGS. 1A-E, FIG. 1A shows an auto injector 100 in a perspective view and FIGS. 1B-E show a close up of some of the different parts of which the auto injector 100 is constituted. In FIGS. 5-7, different cut-through views of the auto injector with a cartridge is shown.

As shown in FIG. 1A, the auto injector 100 is extending from a proximal end 102, which is in contact with the skin of the patient during injection of the medicament and to a distal end 104 pointing away from the needle included in the cartridge.

Figure 7A:
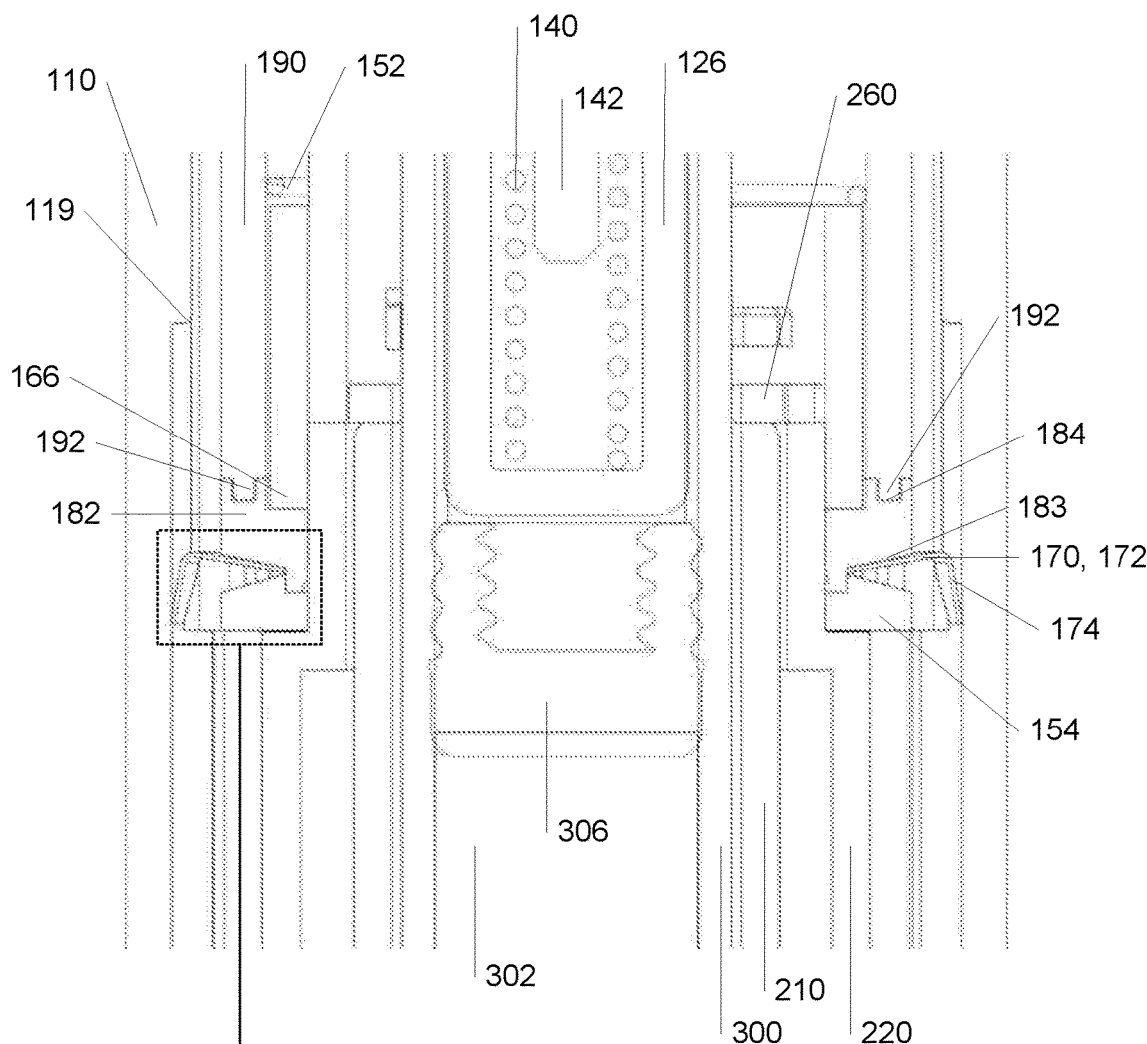
FIGS. 7A-C are close-ups of FIG. 5B.
Figure 7B:
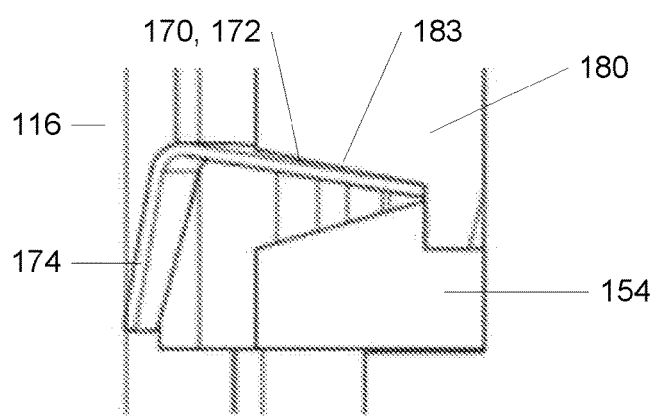
Figure 7C:
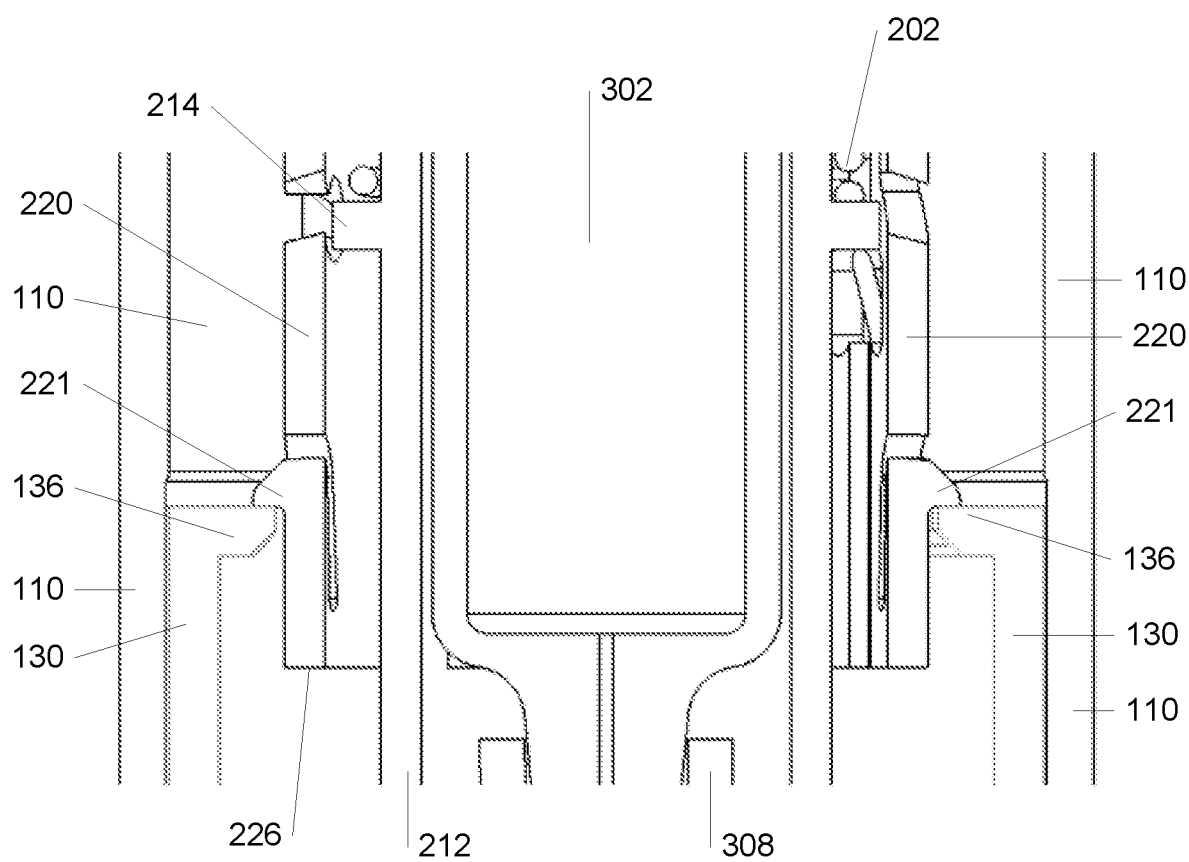

The auto injector 100 comprises a housing 110, and a plunger 120 movably positioned inside the housing 110. At the proximal end 112 of the housing 110 is a housing collar 130. The housing collar 130 comprises a housing collar retention shelf 136 at its distal end 132. The housing collar retention shelf 136 locks the cartridge assembly 200 to an auto injector 100 as shown in FIG. 7C when the cartridge assembly 200 is fully inserted into the auto injector 100. At the proximal end 134 of the housing collar 130 is an outer protruding edge 138, which engages with the proximal end 112 of the housing 110.

Both the housing 110, the plunger 120 and the housing collar 130 has a square like shape at the proximal ends 102, 112, 128, 134. This prevent the parts from rotating relatively to each other. The plunger 120 is allowed to move longitudinally relative to both the housing collar 130 and the housing 110.

The plunger 120 has a ring shaped plunger tube body 124 at its distal end 129. The plunger further has four plunger tube legs 122 extending towards the proximal end 128 of the plunger 120. On each of the plunger tube legs 122 is a proximal plunger surface 121. The proximal plunger surface 121 is positioned on the inside of the plunger 120 as shown in e.g. FIGS. 6A and 6C.

Figures 5A, 5B:
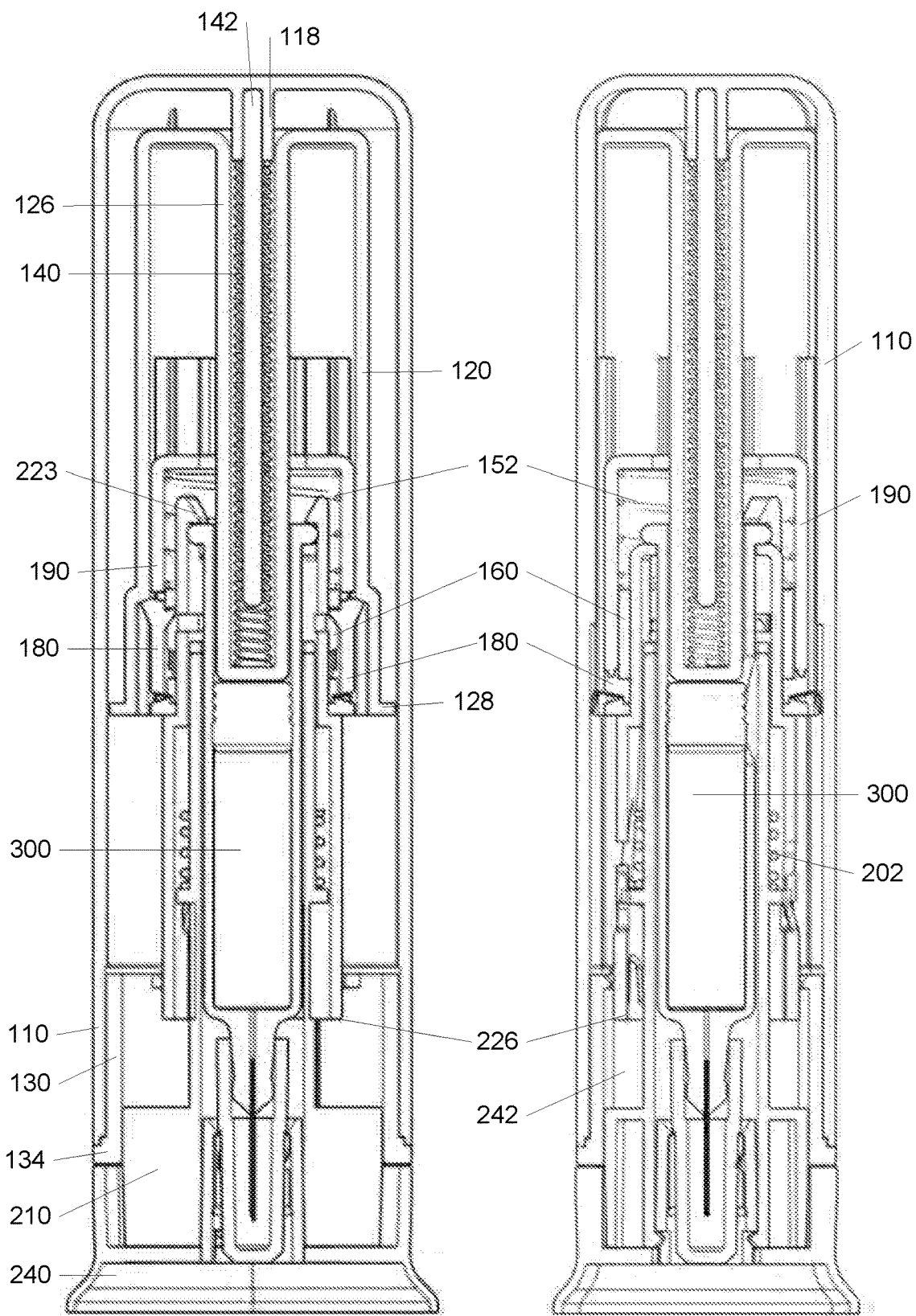
FIG. 5A-B show a cut-through of the auto injector with the cartridge assembly directly after assembly of cartridge and the injector prior to injection of medicament. The view in FIG. 5B is turned approximate 90 degrees compared to the view in FIG. 5A.
Figure 6A:
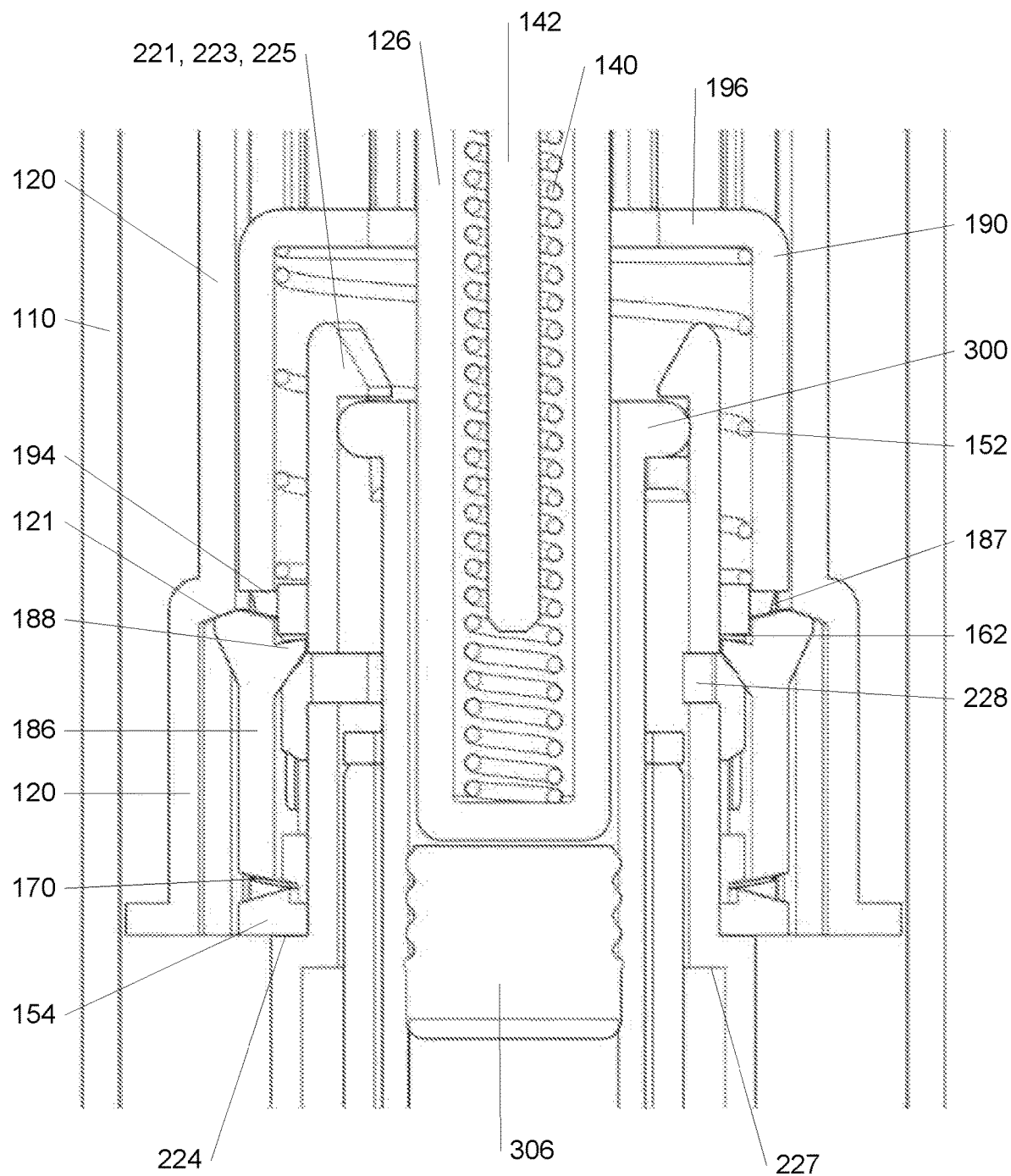
FIGS. 6A-D are close-ups of FIG. 5A.

The auto injector also comprises a plunger spring 140, which moves the plunger 120 proximally during delivery of the medicament. The plunger spring 140 is supported by a plunger spring pin 142, which is positioned inside the plunger spring 140. This is seen in FIGS. 5A-B, in FIGS. 6A-D, which are close-ups of FIG. 5A, and in FIGS. 7A-C, which are close-ups of FIG. 5B.

The plunger spring pin 142 is fixedly positioned at its distal end in a pin holder housing 118 positioned on the inside of the housing 110. By making the housing 110 and the plunger spring pin 142 two separate items, different material properties such as material strength may be used.

The plunger spring 140 is surrounding the plunger spring pin 142. The plunger spring is further supported on its outside by an inner plunger tube part 126 inside which the plunger spring 140 is contained.

Figure 1B:
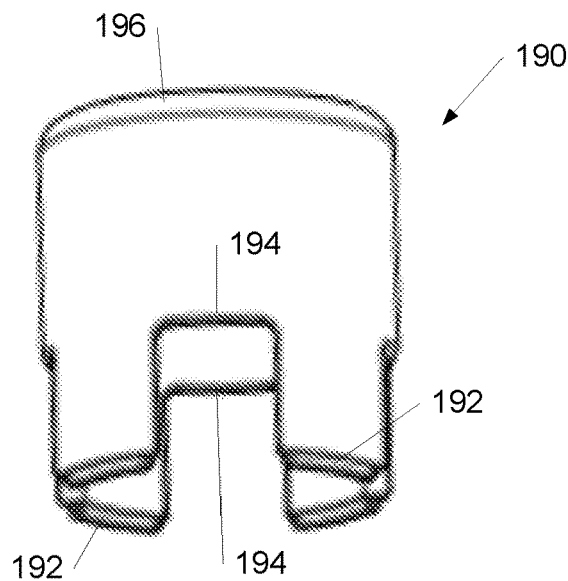
FIGS. 1B-E show a close up of some of the different parts of which the auto injector shown in FIG. 1A is constituted, with FIGS. 1B, 10, 1D, and 1E showing a clutch cap, a clutch lock ring, a clutch release sleeve, and a clutch plate, respectively.
Figure 1C:
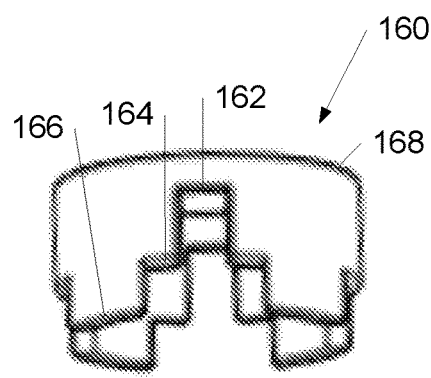
Figure 1D:
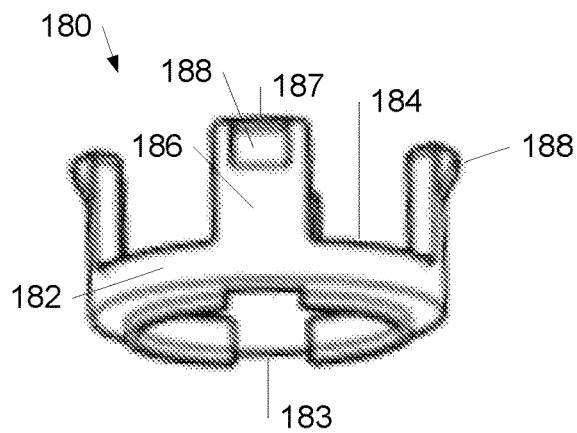
Figure 1E:
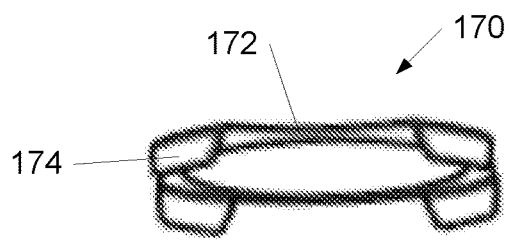

Inside the plunger 120 is a clutch assembly 150, which comprises a clutch cap 190 shown in more details in FIG. 1B, a clutch lock ring 160 shown in more details in FIG. 10, a clutch release sleeve 180 shown in more details in FIG. 1D, and a bi-stable clutch plate 170 shown in more details in FIG. 1E.

The clutch cap 190 comprising a first proximal clutch cap surface 192. The first proximal clutch cap surface 192 is positioned at the proximal end of the clutch cap 190. At the distal end of the clutch cap 190 is a first distal clutch cap surface 196. The length of the clutch cap 190 is defined by the distance between the first proximal clutch cap surface 192 and the first distal clutch cap surface 196.

The clutch cap 190 further comprises a second proximal clutch cap surface 194. The second proximal clutch cap surface 194 is positioned between the first proximal clutch cap surface 192 and the first distal clutch cap surface 196. The difference between the two proximal clutch cap surfaces 192, 194 results in four proximally extending parts on the clutch cap 190. Embodiments where fewer or additional proximally extending parts are present could also be envisioned.

The clutch sleeve 180 comprises a ring shaped part 182 with a distal surface 184 from where release sleeve arms 186 extend. The release sleeve arms 186 of the clutch release sleeve 180 can flex inward upon disengagement of the lock ring 160 from the release sleeve 180. The length of the clutch sleeve 180 extends from a proximal surface 183 on the ring shaped part 182 to a distal surface 187 on the extending release sleeve arm 186.

Figures 6B, 6C, 6D:
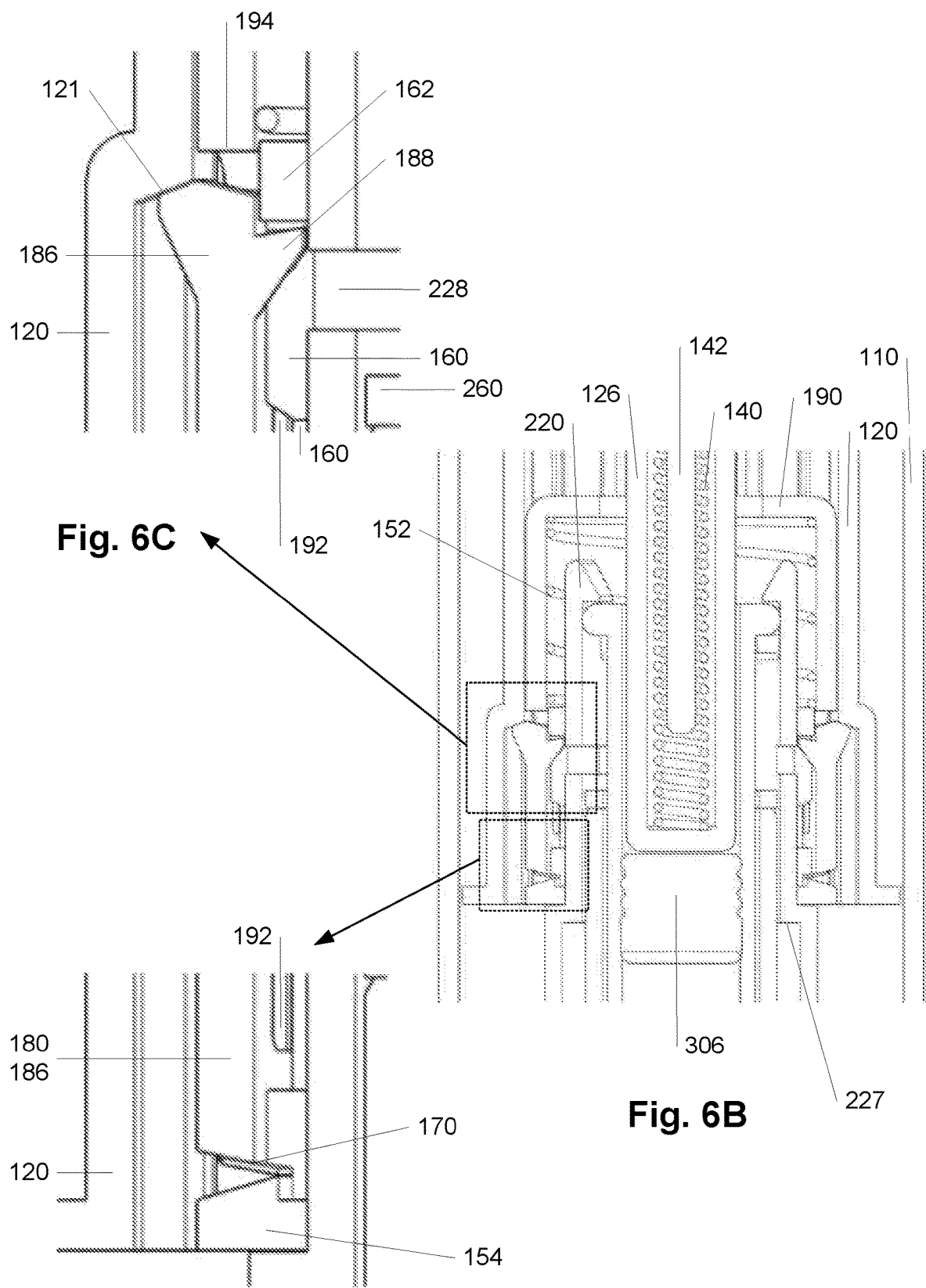

In the assemble state, the release sleeve arms 186 on the release sleeve 180 are pressing against the proximal plunger surface 121 in a first position as shown in FIG. 6C. When the auto injector is assembled, the clutch cap surface 192 is positioned in direct contact with the distal surface 184 on the ring shaped part 182 of the clutch release sleeve 180. This is seen most clearly in FIG. 7A. The two surfaces 184, 192 may also be fixedly connected, e.g. by welding. Alternatively, the clutch cap 190 and the clutch sleeve 180 may be formed as one integrated item.

The clutch lock ring 160 comprises a first proximal clutch lock ring surface 166, a second proximal clutch lock ring surface 164, and a third proximal clutch lock ring surface 162. The clutch lock ring 160 also comprises a distal clutch lock ring surface 168. The length of the third clutch lock ring 160 along a longitudinal direction is defined by distance between the distal clutch lock ring surface 168 and the first proximal clutch lock ring surface 166.

The difference between the first and third clutch lock ring surfaces 166, 162 results in four proximally extending parts on the clutch lock ring 160, which each have stair case plateau defined by the second clutch lock ring surface 164. Embodiments where fewer or additional proximally extending parts are present could also be envisioned. The proximally extending parts on the clutch lock ring 160 and the clutch cap 190 are arranged in parallel as seen in FIG. 7A.

The clutch lock ring 160 is movable in the distal direction relatively to the release sleeve 180 upon movement of the needle shroud 210 of the cartridge assembly 200 distally within the auto injector 100.

The distal surface 184 of the clutch release sleeve 180 is abutting the first proximal clutch lock ring surface 166 when the cartridge assembly 200 and the auto injector 100 are moved towards each other. This can be seen in FIG. 7A, where the distal surface 184 of the ring-shaped part 182 of the clutch release sleeve 180 is in contact with both the first proximal clutch lock ring surface 166 and the first proximal clutch cap surface 192 of the clutch cap 190. The proximal extending parts on the clutch lock ring 160 may move within the openings in the clutch release sleeve 180 defined by the distances between the release sleeve arms 186. This is also seen in FIG. 7A.

Also, the release sleeve arms 186 of the clutch release sleeve 180 can abut the second proximal clutch lock ring surface 164 in a second position.

The release sleeve arms 186 are also adapted for being secured in a locking opening 228 in the cartridge assembly 200 (see FIGS. 5D-E) when flexing inward thereby locking the cartridge assembly 200 and the release sleeve 180 together.

When the release sleeve arms 186 flex inward, the plunger 120 is released thereby enabling the plunger spring 140 to move the plunger 120 proximally for delivery of the medicament. In FIG. 6C, the release sleeve arms 186 is shown prior to unlocking the plunger 120, and in FIGS. 5D-E, the release sleeve arms 186 is shown in the inwardly flexing position allowing the plunger 120 to move proximally.

The auto-injector further comprises a clutch reset spring 152 positioned inside the clutch cap 190 when the auto injector is assembled. The clutch reset spring 152 is exerting a pressure on the clutch cap 190 and the clutch lock ring 160. The lock ring 160 is adapted for compressing the clutch reset spring 152 when the lock ring 160 is moved in the distal direction upon movement of the needle shroud 210 in the cartridge assembly 200 for delivery of the medicament. The clutch reset spring 152 is in turn adapted for pushing the lock ring 160 towards the release sleeve arms 186 after removal of the used syringe 300.

Figure 8A:
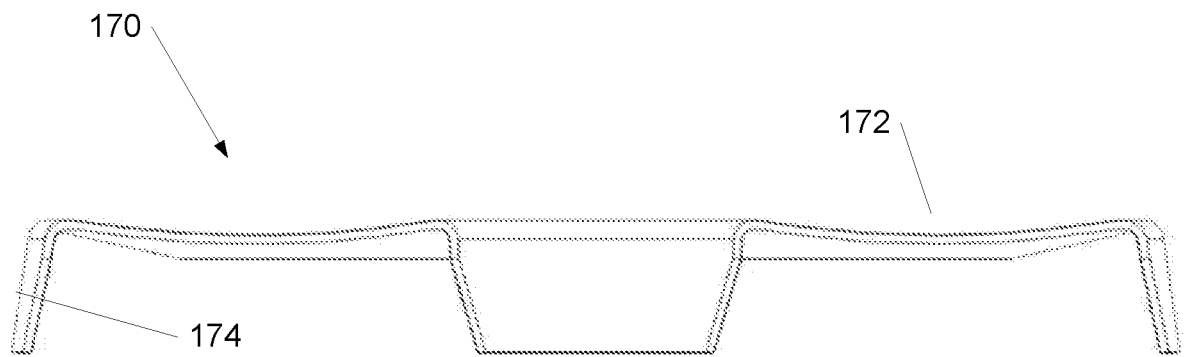
FIGS. 8A-B shows a bi-stable clutch plate in two stable positions.
Figure 8B:
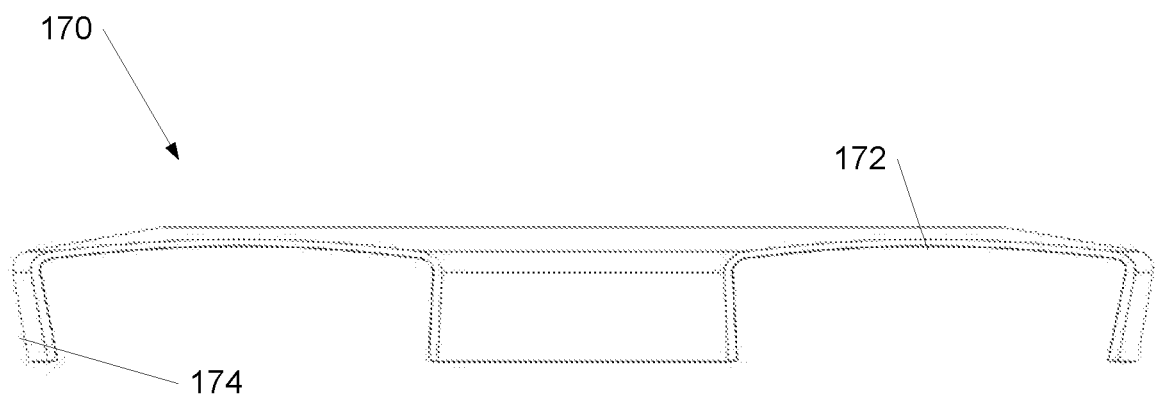

The auto-injector further comprises a bi-stable clutch plate 170 comprising a flexible ring part 172 from where one or more retention arms 174 extend as shown in FIGS. 1E and 8A-B. By bi-stable is meant that the clutch plate 170 has two configurations, which are both stable configurations. Thus, the clutch plate 170 can flex between the two positions. Phrased differently, the flexible ring part 172 is movable between a first stable position and a second stable position. In the first stable position, which is shown in FIGS. 7A-B and 8A, the retention arms 174 engages with an inside surface 116 of the housing 110.

The inside surface of the housing 110 also comprises release ribs 119 as shown in FIG. 7A. When the clutch plate retention arms engages the release ribs 119, the flexible ring part 172 on the clutch plate 170 is moved from the first stable position to the second stable position. In the second stable position, the retention arms 174 are disengaged from the inside surface 116 of the housing 110 allowing the auto injector to be reset. In this position, the retention arms 174 flex inwardly towards the centre of the bi-stable clutch plate 170. This position can be seen in FIG. 8B.

In one or more examples, the clutch plate 170 is in the first stable position when the cartridge assembly 200 and the auto injector 100 are moved towards each other, and wherein the one or more retention arms 174 engaging the inside surface 116 of the housing 110 are ensuring that a spring pressure is held by the clutch plate 170 preventing movement of the clutch assembly 150 and the cartridge assembly 200 within the housing 110, should the relative movement between the cartridge assembly 200 and the auto injector 100 towards each other stop.

In one or more examples, the clutch assembly 150 further comprises a clutch retainer 154 positioned between the clutch plate 170 and the cartridge assembly 200 when the cartridge assembly 200 is contained in the auto injector 100. The clutch retainer 154 can be seen in FIGS. 1A, 6D, and 7B. The clutch retainer 154 may be welded to the clutch release sleeve 180.

Figure 4A:
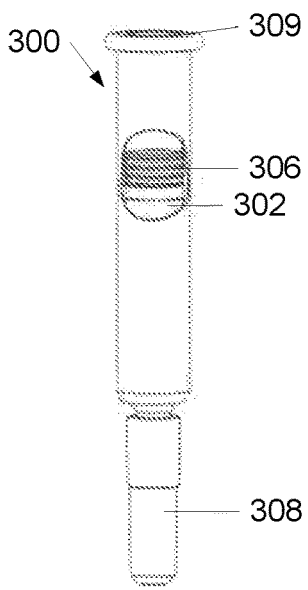
FIGS. 4A-C show the assembly of the syringe and the cartridge assembly (FIG. 4A), the assembly of the auto injector and the cartridge assembly with the syringe (FIG. 4B) and the assembled auto injector and cartridge assembly (FIG. 4C).
Figure 4A:
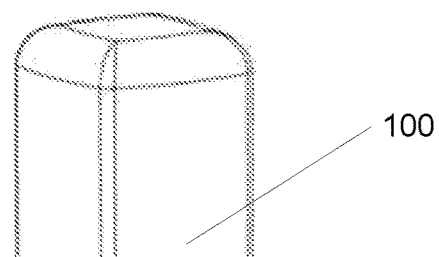
Figure 4A:
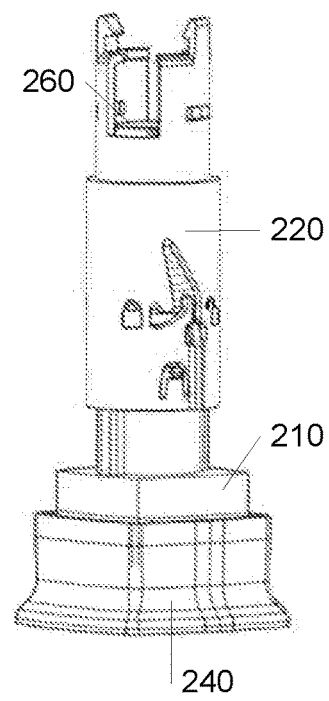
Figure 4B:
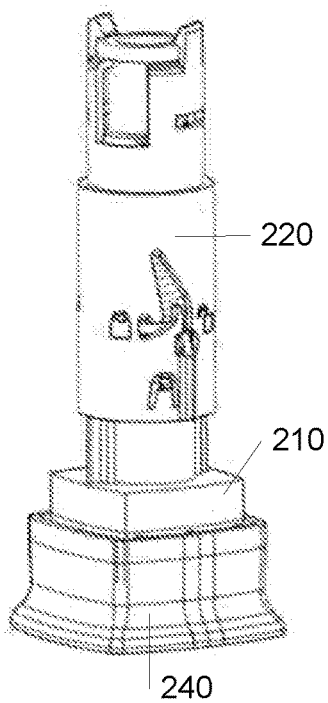
Figure 4C:
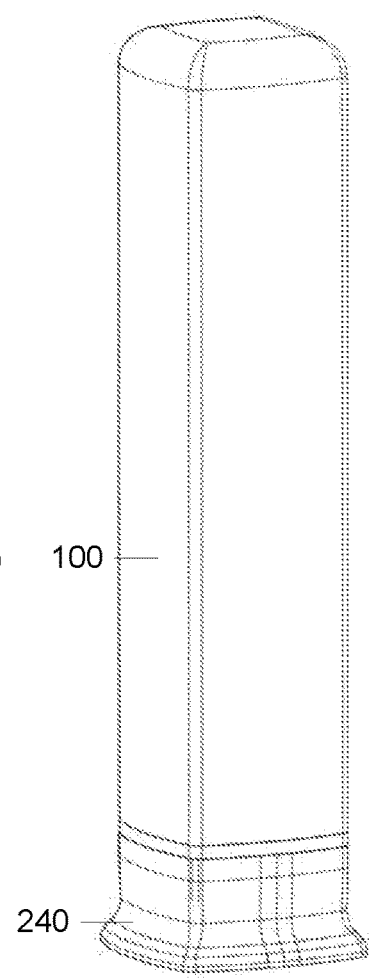

The auto injector 100 is adapted for receiving the cartridge assembly 200 into the proximal end 102 of the auto injector 100 as shown in FIGS. 4A-C. When the cartridge assembly 200 and the auto injector 100 are moved towards each other, the clutch assembly 150 and the plunger 120 are moved in the distal direction relative to the housing 110 whereby the plunger spring 140 is compressed.

After delivery of medicament, the cartridge assembly 200 is movable into the auto injector 100 again. During translation of the cartridge assembly 200 into the auto injector 100, the clutch plate retention arms 174 is brought into contact with release ribs 119 inside the housing (see FIG. 7A) whereby the flexible ring part 172 and the one or more retention arms 174 on the clutch plate 170 are moved from the first stable position to the second stable position. This allows the plunger 120 and the clutch assembly 150 to move proximally within the injector 100 to a reset position. The cartridge assembly 200 is thereby allowed to be removed from the injector 100.

Figure 2:
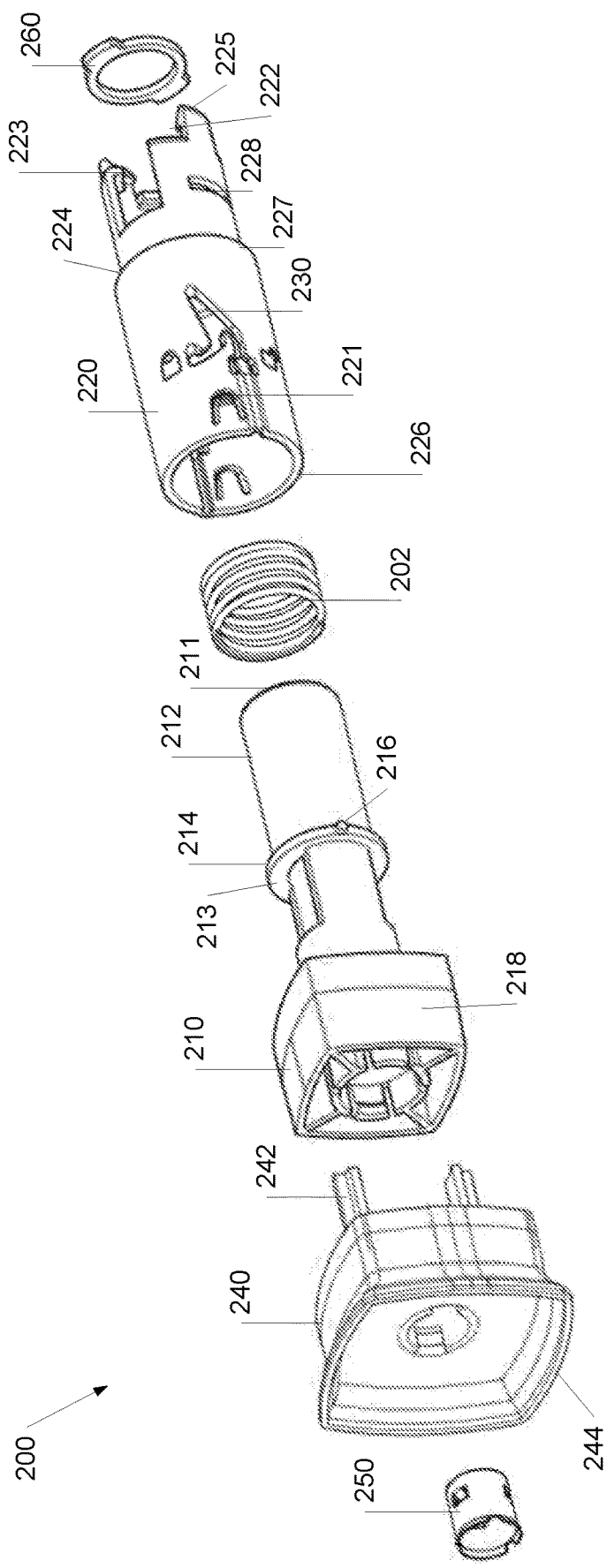
FIG. 2 shows a cartridge assembly for used with an auto injector as shown in FIG. 1A.

FIG. 2 shows a cartridge assembly 200 for use in the auto injector 100 shown in FIGS. 1A-E. The cartridge assembly 200 is adapted for supporting a syringe 300, as can be seen in FIG. 3A or FIG. 4A. The syringe 300 comprises a syringe compartment 302 containing the medicament. A hollow needle 304 through which the medicament can be delivered to a patient is found at the proximal end of the syringe 300. Inside the syringe compartment 302 is a stopper 306, which is movable inside the syringe compartment 302 in the proximal direction, which evacuates the medicament in the syringe compartment 302.

Before delivery of the medicament, the syringe 300 has a syringe cap 308 protecting the needle 304 such that the user does not unintentionally get in contact with the needle 304 during handling and loading of the syringe 300 in the cartridge assembly 200. When injecting the medicament, the stopper 306 inside the syringe compartment 302 is moved proximally by the plunger 120.

As shown in FIG. 2, the cartridge assembly 200 comprises a needle shroud 210 with a hollow elongated tubular section 212 adapted for receiving the syringe 300. The needle shroud 210 also has a peripheral ring protrusion 213 at the end of the tubular section 212. On the ring protrusion 213 is a distal needle shroud support surface 214, and a needle shroud protrusion 216. The needle shroud protrusion 216 is positioned on the ring protrusion 213. At the distal end of the needle shroud 210 is a squared shaped lower needle shroud portion 218.

The cartridge assembly 200 also comprises a lock tube 220 extending around the tubular section 212 of the needle shroud 210. The lock tube 220 extends from a distal end 225 to a proximal end 226 and comprising a snap fit connection 222 adapted for securing the syringe 300 inside the lock tube 220 and the needle shroud 210. In FIGS. 3A-B, the snap fit connection securing the syringe 300 inside the lock tube 220 and the needle shroud 210 is clearly seen. The snap fit connection 222 is at the distal end 225 of the lock tube 220 and comprises inwardly extending flanges 223, which locks the syringe 300 inside the lock tube 220.

The lock tube 220 also comprises one or more retention snaps 221 engaging on the housing collar retention shelf 136 thereby securing the lock tube 220 inside the auto injector 100. This can be seen in FIG. 7C.

The cartridge assembly 200 further comprises a cartridge assembly cap 240 and a grip tube 250. The grip tube 250 is positioned inside the cartridge assembly cap 240 at its proximal end 244, and is adapted for capturing the syringe cap 308 when the syringe 300 is positioned inside the cartridge assembly 200. This is seen in FIG. 3A. The grip tube 250 and the cartridge assembly cap 240 are shown as two separate items in the figures, but could also be formed as integral items.

The cartridge assembly cap 240 comprises distally protruding tabs 242 abutting the proximal end 226 of the lock tube 220 thereby preventing proximal movement of the lock tube 220 relative to the needle shroud 210 when the cartridge assembly cap 240 is connected with the needle shroud 210. This is seen in FIG. 5B.

Figure 5C:
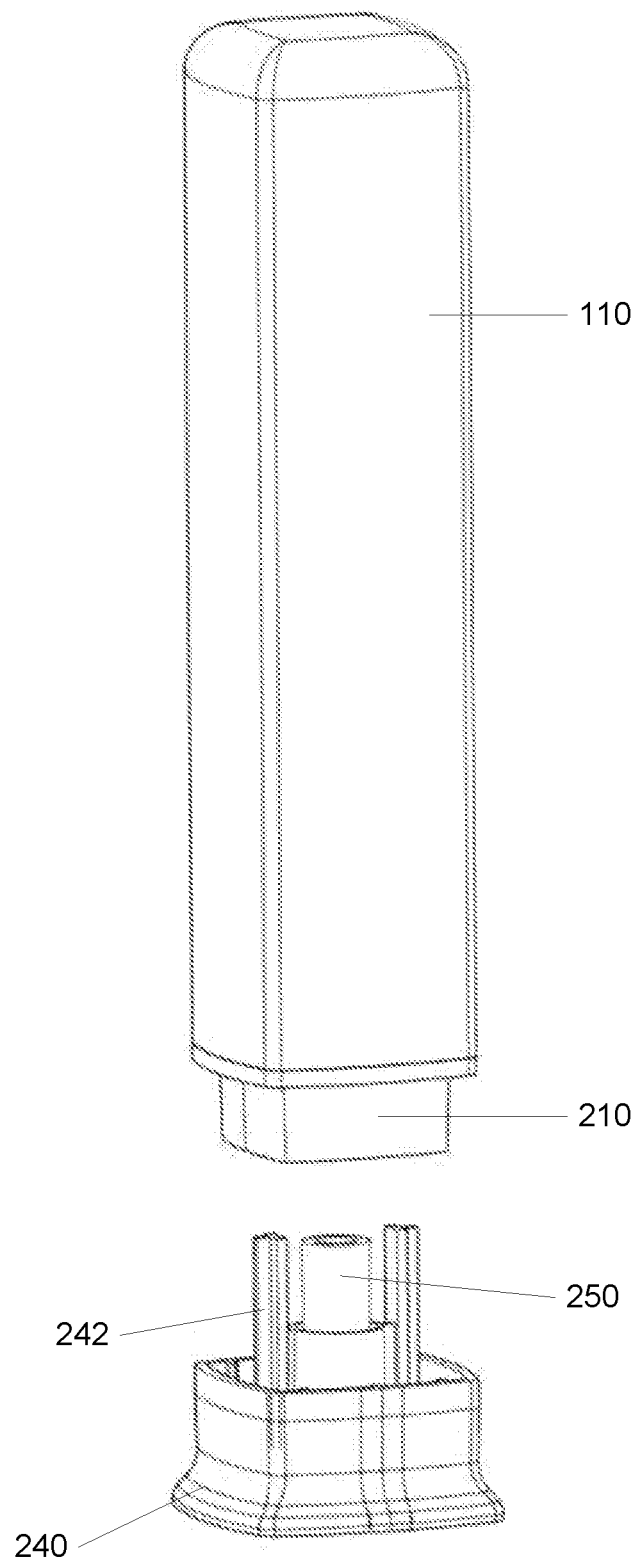
FIG. 5C shows the auto injector after removal of the cartridge assembly cap where the auto injector is ready for injection.

The cartridge assembly cap 240 and the grip tube 250 are removable from the cartridge assembly 200 after the cartridge assembly 200 is fully inserted into the auto injector 100. In this manner, the syringe cap 308 can be removed thereby exposing the needle 304 without the user getting in contact with the needle 304 directly, as the grip tube 250 pulls the syringe cap 308 away from the syringe 300 when the assembly cap 240 is removed. This is shown in FIG. 5C.

When the cartridge assembly cap 240 is removed, the needle shroud 210 is enabled for retracting into the housing 110. The retraction of the needle shroud 210 inside the housing 110 is normally obtained by depression of the housing 110 proximally towards the needle shroud 210. Upon depression of the housing 110, the lock tube 220 comprising the syringe 300 moves proximally together with the housing 110 enabling insertion of the needle 304 as shown in FIG. 5D.

When the housing 110 is depressed, the needle shroud 210 rotates the lock tube 220 at least partly relatively to the housing 110, as the needle shroud 210 translates distally into the housing 110.

Figures 5D, 5E:
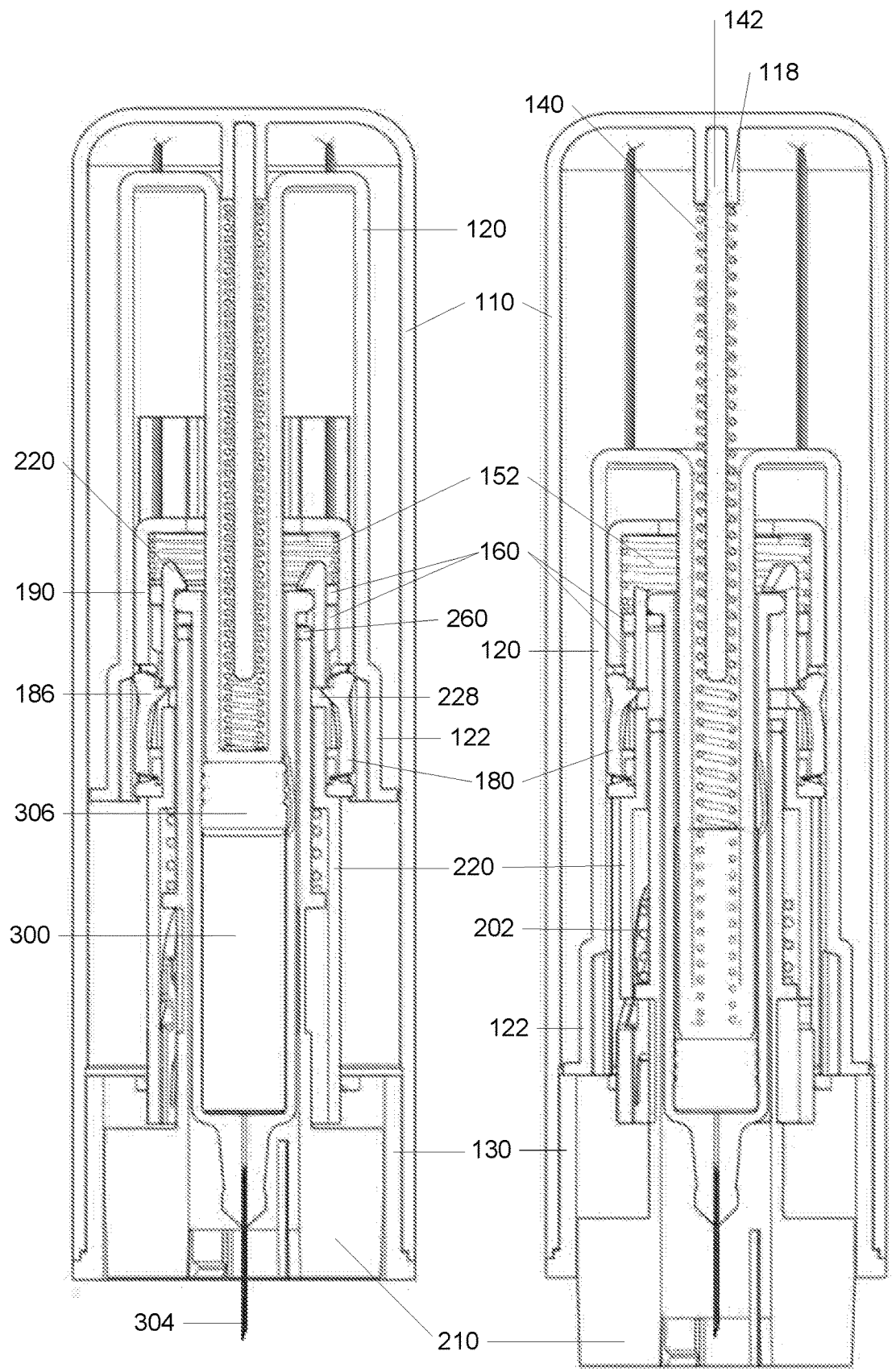
FIG. 5D show a cut-through of the auto injector with the cartridge assembly directly after insertion of the needle but prior to injection of medicament.
FIG. 5E show a cut-through of the auto injector with the cartridge assembly after injection of medicament.

Upon depression of the housing 110, the release collar 260 also pushes the clutch lock ring 160 distally allowing the release sleeve arms 186 on the clutch release sleeve 180 to flex inward as shown in FIGS. 5D-E. The plunger 120 is normally released when the lock ring 160 is moved distally within the clutch assembly 150. The lock ring 160 is moved by the release collar 260, which in turn is normally moved by the needle shroud 210 during needle insertion.

After insertion of the needle 304 due to depression of the housing 110, the plunger 120 moves the stopper 306 inside the syringe 300 proximally whereby the medicament is delivered to the patient. FIG. 5D shows the situation where the needle 304 has been inserted, but the medicament is yet to be delivered.

After release of plunger 120, the lock tube 220 is adapted for completing the rotation relatively to the housing 110 whereby the one or more lock tube retention snaps 221 are moved to a position allowing removal of the cartridge assembly 200 from the auto injector 100.

The cartridge assembly 200 also comprises a release collar 260 as shown in FIGS. 2 and 3A. The release collar 260 is positioned against a distal surface 211 of the needle shroud 210.

The lock tube 220 comprises a lock tube channel 230 as shown in FIG. 3B. The lock tube channel 230 comprises three positions; a first lock tube channel position 231, a second lock tube channel position 232, and a third lock tube channel position 233.

As most clearly seen in FIG. 2, the needle shroud 210 comprises a needle shroud protrusion 216. The needle shroud protrusion 216 is movable inside the lock tube channel 230 between the three positions 231, 232, 233. The needle shroud protrusion 216 is in the first lock tube channel position 231 before removal of the cartridge assembly cap 240.

Upon depression of the housing 110 after removal of the cartridge assembly cap 240, the needle shroud protrusion 216 is moved from the first lock tube channel position 231 to the second lock tube channel position 232. Inside the cartridge assembly is a lock tube spring 202, which is positioned around the hollow elongated tubular section 212 of the needle shroud 210. The lock tube spring 202 is positioned between a peripheral distal needle shroud support surface 214 on the needle shroud 210 and a proximal lock tube support surface 227 on the lock tube 220. The lock tube spring 202 is compressed during delivery of the medicament as the lock tube 220 and the needle shroud 210 moves towards each other.

After delivery of the medicament, the lock tube spring 202 is allowed to decompress when the auto injector 100 is removed from the patient. The decompression of the lock tube spring 202 moves the needle shroud 210 in the proximal direction relative to the lock tube 220. This moves the needle shroud 210 to a position where it covers the needle 304 as shown in FIG. 5E. The decompression of the lock tube spring 202 also moves the needle shroud protrusion 216 from the second lock tube channel position 232 to the third lock tube channel position 233. When the needle shroud protrusion 216 is in the third lock tube channel position 233 compression of the needle shroud relative to the lock tube 220 is limited- or prevented. This ensures that the user is prevented from getting in contact with the needle 304 after injection. Further, it allows the cartridge assembly 200 to be pushed deeper into the housing 110 allowing the clutch plate 170 to be flipped to the second stable position for cartridge assembly 200 removal and auto injector 100 reset.

Figure 5F:
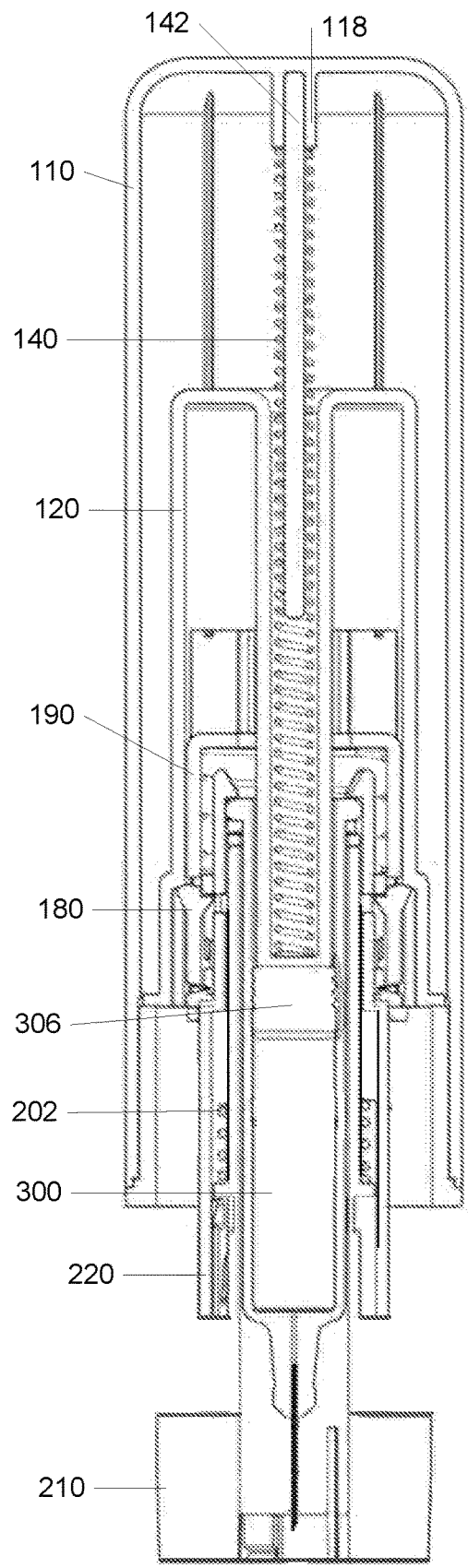
FIG. 5F shows a cut-through of the auto injector with the cartridge assembly partly removed.

When the lock tube 220 rotates relatively to the housing 110, the one or more lock tube retention snaps 221 on the lock tube 220 are moved to a position allowing removal of the used cartridge assembly 200 from the auto injector 100. This is shown in FIG. 5F.

By pushing the cartridge assembly 200 into the housing 110 after the needle shroud 210 has been locked out when the needle shroud protrusion 216 is moved to the third position 233 in the lock tube channel 230. This ejects the cartridge assembly 200 from the housing 110. The release sleeve arms 186 flex outward towards the end of cartridge assembly 200 removal. It can been seen that the release sleeve arm 186 has flexed outward whereby it is no longer locked inside the locking opening 228 in the lock tube 220. Thus, the cartridge assembly 200 is no longer locked to the injector 100.

REFERENCES 100 auto injector
102 proximal end of the auto injector
104 distal end of the auto injector
110 housing
112 proximal end of the housing
114 distal end of the housing
116 inside surface of the housing
118 pin holder housing
119 release ribs inside the housing
120 plunger
121 proximal plunger surface
122 plunger tube leg
124 ring shaped plunger tube body
126 inner plunger tube part
128 proximal end of the plunger
129 distal end of the plunger
130 housing collar
132 distal end of the housing collar
134 proximal end of the housing collar
136 housing collar retention shelf
138 outer protruding edge on the housing collar
140 plunger spring
142 plunger spring pin
150 clutch assembly
152 clutch reset spring
154 clutch retainer
160 clutch lock ring
162 third proximal clutch lock ring surface
164 second proximal clutch lock ring surface
166 first proximal clutch lock ring surface
168 distal clutch lock ring surface
170 clutch plate
172 flexible ring part on the clutch plate
174 retention arms extending from the flexible ring part
180 clutch release sleeve
182 ring shaped part
183 proximal surface on the ring shaped part
184 distal surface on the ring shaped part
186 release sleeve arm
187 distal surface on the extending release sleeve arm
188 locking arm protrusion on the extending release sleeve arm
190 clutch cap
192 first proximal clutch cap surface
194 second proximal clutch cap surface
196 first distal clutch cap surface
200 cartridge assembly
202 lock tube spring
210 needle shroud
211 distal surface/distal end of the needle shroud
212 hollow elongated tubular section of the needle shroud
213 peripheral ring protrusion
214 needle shroud support surface
216 needle shroud protrusion
218 squared shaped lower needle shroud portion
220 lock tube
221 retention snap
222 snap fit connection on lock tube
223 inwardly extending flanges on the lock tube
224 distal lock tube support surface
225 distal end of the lock tube
226 proximal end of the lock tube
227 proximal lock tube support surface
228 locking opening
229 second proximal lock tube support surface
230 lock tube channel
231 first lock tube channel position
232 second lock tube channel position
233 third lock tube channel position
240 cartridge assembly cap
242 distally protruding tabs of the cartridge assembly cap
244 proximal end of the cartridge assembly cap
250 grip tube
260 release collar
300 syringe
302 syringe compartment containing the medicament
304 hollow needle
306 stopper
308 syringe cap

The invention claimed is:

1. An auto injector for delivery of a medicament to a patient, the auto injector extending from a proximal end to a distal end, wherein the auto injector is adapted for receiving a cartridge assembly supporting a syringe comprising:
a syringe compartment containing the medicament;
a hollow needle through which the medicament can be delivered to a patient;
a stopper proximally movable inside the syringe compartment for evacuating the medicament in the syringe compartment; and
a syringe cap adapted for protecting the needle; and
wherein the auto injector comprises:
a housing defining a passageway formed by an inside surface of the housing and further including release ribs extending from the inside surface and into the passageway;
a plunger movably positioned in the passageway of the housing, the plunger being adapted for moving the stopper inside the syringe compartment proximally for delivery of the medicament;
a plunger spring between the housing and the plunger, and adapted for moving the plunger proximally for delivery of the medicament; and
a clutch assembly positioned in the passageway of the housing, the clutch assembly comprising a bi-stable clutch plate comprising a flexible ring part and one or more retention arms, the flexible ring part defining a radius and being movable between a first stable position during delivery of medicament and a second stable position, wherein a free end of the one or more retention arms extend radially outward from an outer perimeter of the flexible ring part and are engaged with the inside surface of the housing in the first stable position, and wherein the free end of the one or more retention arms extend radially inward from the outer perimeter of the flexible ring part and are disengaged from the inside surface of the housing in the second stable position, wherein the one or more retention arms extend at a first angle in the first stable position and the one or more retention arms extend at a second angle in the second stable position, and
wherein upon translation of the cartridge assembly into the auto injector after delivery of the medicament, the one or more retention arms are brought into contact with the release ribs and the flexible ring part is moved from the first stable position to the second stable position allowing the cartridge assembly to be removed and the auto injector to be reset.

2. The auto injector according to claim 1, wherein the clutch assembly further comprises:

a clutch release sleeve comprising a ring shaped part with a distal surface from where release sleeve arms extend; and a clutch lock ring comprising a first proximal clutch lock ring surface, and a second proximal clutch lock ring surface, wherein the distal surface of the clutch release sleeve is adapted for abutting the first proximal clutch lock ring surface in a first position and is adapted for abutting the second proximal clutch lock ring surface in a second position.

3. The auto injector according to claim 2, wherein the release sleeve arms on the release sleeve are further pressing against a proximal plunger surface of the plunger in the first position.

4. The auto injector according to claim 2, wherein the clutch lock ring is movable in the distal direction relative to the release sleeve upon movement of the cartridge assembly distally within the auto injector.

5. The auto injector according to claim 2, wherein the release sleeve arms of the clutch release sleeve are adapted for flexing inward upon disengagement of the clutch lock ring from the release sleeve.

6. The auto injector-according to claim 2 further comprising:
a clutch cap comprising a first proximal clutch cap surface abutting the distal surface on the ring shaped part of the clutch release sleeve; and
a clutch reset spring positioned inside the clutch cap exerting a pressure on the clutch cap and the clutch lock ring.

7. The auto injector according to claim 2, wherein the flexible ring part of the bi-stable clutch plate abuts against a proximal surface of the ring shaped part of the clutch release sleeve in the first stable position.

8. The auto injector according to claim 1, wherein the clutch plate is in the first stable position when the cartridge assembly and the auto injector are moved towards each other, and wherein the one or more retention arms engaging the inside surface of the housing are ensuring that a spring pressure is held by the clutch plate preventing movement of the clutch assembly within the housing, should the relative movement between the cartridge assembly and the auto injector towards each other stop.

9. The auto injector according to claim 1, further comprising a housing collar positioned at the proximal end of the housing partly extending inside the housing, wherein the housing collar comprises a housing collar retention shelf at its distal end, the housing collar retention shelf being adapted for locking the cartridge assembly to the auto injector when the cartridge assembly is fully inserted into the auto injector.

10. The auto injector according to claim 1, wherein the clutch assembly further comprises a clutch retainer positioned between the clutch plate and the cartridge assembly when the cartridge assembly is contained in the auto injector.

11. The auto injector according to claim 1, further comprising a plunger spring pin connected to the housing and extending inside an inner plunger tube part, wherein the plunger spring is surrounding the plunger spring pin.

12. The auto injector according to claim 1, wherein when the cartridge assembly and the auto injector are moved towards each other, the clutch assembly and the plunger are moved in the distal direction relative to the housing whereby the plunger spring is compressed.

13. The auto injector according to claim 1, wherein the one or more retention arms extend from the outer perimeter and pivot between the first and second stable positions.

14. An auto injector system comprising the auto injector according to claim 1 and a cartridge assembly for use in the auto injector, wherein the cartridge assembly is adapted for supporting a syringe comprising:
a syringe compartment containing the medicament;
a hollow needle-through which the medicament can be delivered to a patient;
a stopper proximally movable inside the syringe compartment for evacuating the medicament in the syringe compartment;
a syringe cap adapted for protecting the needle;
wherein the cartridge assembly comprises:
a needle shroud comprising a hollow elongated tubular section adapted for receiving the syringe; and
a lock tube extending around the tubular section of the needle shroud, the lock tube comprising a snap fit connection adapted for securing the syringe inside the lock tube and the needle shroud.

15. The auto injector system according to claim 14, wherein the distal end-of the lock tube comprises inwardly extending flanges, which locks the syringe inside the lock tube with the snap fit connection.

16. The auto injector system according to claim 14, wherein the cartridge assembly further comprises a cartridge assembly cap and a grip tube, wherein the grip tube is positioned inside the cartridge assembly cap, and wherein the grip tube is adapted for capturing the syringe cap when the syringe is positioned inside the cartridge assembly.

17. The auto injector system according to claim 14, further comprising a housing collar positioned at the proximal end of the housing partly extending inside the housing, wherein the housing collar comprises a housing collar retention shelf at its distal end, the housing collar retention shelf being adapted for locking the cartridge assembly to the auto injector when the cartridge assembly is fully inserted into the auto injector, and wherein the lock tube comprises one or more retention snaps engaging on the housing collar retention shelf securing the lock tube inside the auto injector.

18. The auto injector system according to claim 17, wherein upon depression of the housing, the lock tube comprising the syringe is adapted for moving proximally together with the housing enabling insertion of the needle.

19. The auto injector system according to claim 14, wherein the lock tube comprises a lock tube channel and the needle shroud comprises a needle shroud protrusion movable inside the lock tube channel between:
a first lock tube channel position,
a second lock tube channel position, and
a third lock tube channel position.

20. The auto injector system according to claim 14, wherein the cartridge assembly further comprises a lock tube spring positioned between a peripheral distal needle shroud support surface and a proximal lock tube support surface.

21. An auto injector for delivery of a medicament to a patient, the auto injector extending from a proximal end to a distal end, wherein the auto injector is adapted for receiving a cartridge assembly supporting a syringe comprising:
a syringe compartment containing the medicament;
a hollow needle through which the medicament can be delivered to a patient;
a stopper proximally movable inside the syringe compartment for evacuating the medicament in the syringe compartment; and
a syringe cap adapted for protecting the needle; and
wherein the auto injector comprises:
a housing;

a plunger movably positioned inside the housing, the plunger being adapted for moving the stopper inside the syringe compartment proximally for delivery of the medicament;

a plunger spring adapted for moving the plunger proximally for delivery of the medicament;

a clutch assembly positioned inside the housing, the clutch assembly comprising a clutch release sleeve comprising a ring shaped part with a distal surface from where release sleeve arms extend;

a clutch lock ring comprising a first proximal clutch lock ring surface, and a second proximal clutch lock ring surface, wherein the distal surface of the clutch release sleeve are adapted for abutting the first proximal clutch lock ring surface in a first position and the second proximal clutch lock ring surface in a second position; and a bi-stable clutch plate comprising a flexible ring part from where one or more retention arms extend, the flexible ring part being movable between:

a first stable position where the one or more retention arms protrude outwardly and engages with an inside surface of the housing, wherein the flexible ring part is in the first stable position during delivery of medicament, and a second stable position where the one or more retention arms protrude inwardly and are disengaged from the inside surface of the housing, and wherein upon translation of the cartridge assembly into the auto injector after delivery of the medicament, the one or more retention arms are brought into contact with release ribs inside the housing whereby the flexible ring part on the clutch plate is moved from the first stable position to the second stable position allowing the cartridge assembly to be removed and the auto injector to be reset.

22. The auto injector according to claim 21, wherein the release sleeve arms on the release sleeve are further pressing against a proximal plunger surface of the plunger in a first position.

23. The auto injector according to claim 21, wherein the clutch lock ring is movable in the distal direction relative to the release sleeve upon movement of the cartridge assembly distally within the auto injector.

24. The auto injector according to claim 21, wherein the release sleeve arms of the clutch release sleeve are adapted for flexing inward upon disengagement of the clutch lock ring from the release sleeve.

25. The auto injector according to claim 21, wherein the flexible ring part of the bi-stable clutch plate abuts against a proximal surface of the ring shaped part of the clutch release sleeve in the first stable position.

* * * * *